(12) United States Patent
Håkansson (10) Patent No.: US 10,792,190 B2
(45) Date of Patent: *Oct. 6, 2020

(54) HEARING PROTECTOR AND A METHOD OF MAKING A HEARING PROTECTOR

(71) Applicant: 3M INNOVATIVE PROPERTIES COMPANY, St. Paul, MN (US)

(72) Inventor: Johan Håkansson, Vaxjo (SE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/838,486

(22) Filed: Apr. 2, 2020

(65) Prior Publication Data

US 2020/0246189 A1 Aug. 6, 2020

Related U.S. Application Data

(63) Continuation of application No. 16/090,293, filed as application No. PCT/US2017/026403 on Apr. 6, 2017, now Pat. No. 10,639,201.

(30) Foreign Application Priority Data

Apr. 8, 2016 (EP) ..................................... 16164349

(51) Int. Cl.
*A61F 11/14* (2006.01)
*H04R 1/10* (2006.01)

(52) U.S. Cl.
CPC ............ *A61F 11/14* (2013.01); *H04R 1/1008* (2013.01); *H04R 1/1058* (2013.01);
(Continued)

(58) Field of Classification Search
CPC .. A61F 11/14; A61F 2011/145; H04R 1/1008; H04R 1/1041; H04R 1/1058; H04R 1/1083; H04R 2430/01
(Continued)

(56) References Cited

U.S. PATENT DOCUMENTS 6,466,681 B1 10/2002 Siska
8,243,943 B2 8/2012 Nordin
(Continued)

FOREIGN PATENT DOCUMENTS

CA 2243728 1/2000
EP 1689337 3/2009
(Continued)

OTHER PUBLICATIONS

International Search Report for PCT International Application No. PCT/US2017/026403, dated Aug. 4, 2017, 5 pages.

*Primary Examiner* — Vivian C Chin
*Assistant Examiner* — Friedrich Fahnert
(74) *Attorney, Agent, or Firm* — Katherine M. Scholz (57) ABSTRACT

A hearing protector having an ear cup forming a space for a wearer's ear. The ear cup has a shell with an ear facing inner side and a passageway extending through the shell between the ear facing inner side and an outer side of the shell. The ear cup further has a loudspeaker assembly which seals the passageway from the outer side. The loud speaker assembly further has a seal member and a loudspeaker module. A portion of the seal member is arranged between the shell and a fastener, and the fastener retains the loudspeaker assembly at the shell. The hearing protector facilitates manufacturing and maintenance and provides for maximize wearing comfort and technical reliability.

13 Claims, 4 Drawing Sheets

(52) U.S. Cl.
CPC ...... *H04R 1/1083* (2013.01); *A61F 2011/145* (2013.01); *H04R 1/1041* (2013.01); *H04R 2430/01* (2013.01)

(58) Field of Classification Search
USPC .................................. 381/72, 73.1, 74, 104
See application file for complete search history.

(56) References Cited

U.S. PATENT DOCUMENTS

| | | | |
|---|---|---|---|
| 8,750,552 | B2 | 6/2014 | Baringa |
| 9,131,310 | B2 | 9/2015 | Sjoman |
| 2003/0182713 | A1* | 10/2003 | Rolla ............... A61F 11/14 2/209 |
| 2005/0126845 | A1* | 6/2005 | Vaudrey ............ A61F 11/14 181/129 |
| 2007/0274529 | A1 | 11/2007 | Nordin |
| 2008/0279409 | A1 | 11/2008 | Hupkes |
| 2010/0166246 | A1 | 7/2010 | Zeng |
| 2011/0064239 | A1 | 3/2011 | Sjoman |
| 2013/0003984 | A1 | 1/2013 | Belafonte |
| 2013/0170691 | A1 | 7/2013 | Baringa |
| 2014/0211959 | A1 | 7/2014 | Boyajian |
| 2017/0245787 | A1 | 8/2017 | Brown |

FOREIGN PATENT DOCUMENTS

| | | |
|---|---|---|
| EP | 2677766 | 12/2013 |
| GB | 2339642 | 2/2000 |
| NL | 1009810 | 4/2000 |
| WO | WO 2005-051255 | 6/2005 |
| WO | WO 2006-058319 | 6/2006 |
| WO | WO 2009-139682 | 11/2009 |

\* cited by examiner

HEARING PROTECTOR AND A METHOD OF MAKING A HEARING PROTECTOR

CROSS REFERENCE TO RELATED APPLICATIONS

This application is a continuation of U.S. application Ser. No. 16/090,293, filed Oct. 1, 2018, which is a national stage filing under 35 U.S.C. 371 of PCT/US2017/026403, filed Apr. 8, 2016, which claims the benefit of EP Application No. 1614349.9, filed Apr. 8, 2016, the disclosure of which is incorporated by reference in its entirety herein.

TECHNICAL FIELD

This disclosure relates to a hearing protector having an ear cup with a shell forming an ear facing inner side and an outer side.

BACKGROUND ART

Hearing protectors are typically used in noisy environments for protecting a wearer's hearing from noise at potentially harmful noise levels. Typically, hearing protectors have two muffs or caps which cover the ears of the wearer and which are connected to one another by a headband. Each cup further typically is formed by a rigid shell that is furnished with a noise dampening material, for example a foamed material.

There is a general desire to make hearing protectors user-friendly, in particular to encourage persons that are in noisy environments for longer times to actually wear the protectors. While noise dampening is the essential purpose of a hearing protector, there is often a need for the wearer to hear certain sounds from the environment, like acoustic signals, instructions, or conversations. Further, there is often a desire for the wearer to use the hearing protector as headset for radio or telephone applications.

There are active hearing protectors on the market which have passive noise dampening properties and additionally are configured to transmit sounds from the environment into the ear cup via active electronics connected to a microphone outside the ear cup and a loud speaker inside the ear cup. Such hearing protectors are typically set up so that the active sound transmission is restricted to a pre-determined level with respect to the human hearing.

Sound levels from the environment that exceed that pre-determined level are dampened due to the passive dampening properties of the hearing protector.

WO 2006/058319 for example discloses a hearing protector device including a sound attenuating body and an electronic unit having a microphone, an amplifier, and a loudspeaker, where the electronic unit is selectively activated and, when activated, receives sound from an ambient environment, amplifies a frequency range of the received sound corresponding to a frequency range of human speech, and varies said amplification such that a total level of sound passing through the body and through the electronic unit does not exceed a maximum predetermined sound level.

Although existing active hearing protectors have a variety of advantages there is still a need for a hearing protector which is of preferably high quality and durable but relatively inexpensive. Further, such a hearing protector desirably can be serviced relatively conveniently.

SUMMARY

This disclosure relates to a hearing protector having an ear cup forming a space for a wearer's ear. In particular, the disclosure relates to the ear cup. The ear cup comprises a shell having an ear facing inner side and a passageway extending through the shell between the ear facing inner side and an outer side of the shell. The ear cup further comprises a loudspeaker assembly which seals the passageway from the outer side. The loud speaker assembly comprises a seal member and a loudspeaker module, wherein at least a (preferably circumferential) portion of the seal member is arranged between the shell and a fastener which retains the loudspeaker assembly at the shell.

The design may be advantageous in that it provides a hearing protector which is relatively comfortable to wear. Further the design may be advantageous in that it provides a hearing protector which is relatively reliable in use. The hearing protector may further be manufactured at relatively low costs.

The shell of the ear cup generally has an ear facing end and an opposite rear end that faces away from a wearer's ear (when the hearing protector is worn). The ear facing inner side is typically arranged adjacent the ear facing end. A ring-shaped cushioning is preferably arranged adjacent the ear facing end. Further a noise absorber pad is arranged between the cushioning and the ear facing inner side of the shell. The shell may be furnished with alternative or additional noise absorber means. The cushioning and the noise absorber pad in combination preferably provide the space for the wearer's ear.

The cushioning comprises a soft and resilient core material, for example a foamed plastic material and is preferably covered by a sheath. The sheath may be made of a soft film material that is optionally generally non-permeable relative to moisture. The cushioning provides for the ear cup to seal at a wearer's head so as to hermetically encapsulate the space around the wearer's ear. Thus, a so-called passive noise dampening or attenuation is provided by the ear cup.

According to the present disclosure, the loudspeaker module is preferably arranged at the outer side of the shell. It has been found that in such an arrangement the reliability of the loudspeaker module can be maximized. Although hearing protectors are often used in harsh environments so that there is a general desire to accommodate electronic components preferably inside the shell, it has been found that the arrangement on the outside has certain advantages. In particular, the outside arrangement provides for the loudspeaker module to be protected from moisture that may be in the air of the encapsulated space provided by the ear cup, for example due to sweating of the wearer during wearing of the hearing protector. Further, the outside arrangement prevents the loudspeaker module from heating up the air in encapsulated space.

In one embodiment the seal member forms a cavity. The loudspeaker is preferably accommodated in this cavity. The cavity is dimensioned so that the loudspeaker module fills a partial volume of the cavity but a further partial volume of the cavity provides a sound volume. The sound volume allows for determining a frequency profile of the sound provided by the loudspeaker assembly.

In a further embodiment the seal member is shaped as a tray. In particular, the seal member has a circumferential side wall and a base wall. The base wall forms an ear facing end of the seal member. The seal member further forms an open end opposite of the ear facing end.

In a further embodiment the seal member has an aperture through the seal member. The loudspeaker module preferably closes the aperture. Preferably, the passageway in the shell and the aperture in the seal member overlap. In particular the aperture and the passageway are preferably in fluid communication.

In a further embodiment the fastener sealingly covers the open end of the seal member. In particular, the fastener may hermetically seal or cover the partial cavity forming the sound volume. The fastener may have at least one through-hole in fluid communication with the sound volume. Thus, the hearing protector may be used at different environmental pressure conditions (for example at different altitudes) without affecting the sound frequency profile of the loudspeaker assembly. This is because air can exchange between the sound volume and the exterior.

In one embodiment the seal member tapers from the open end toward the ear facing end. This enables for play-free and thus accurately fitting of the seal member in a correspondingly shaped structure (for example a recess) in the shell.

In a further embodiment the shell of the ear cup has a compartment which opens in a direction away from the ear space. The seal member is preferably arranged at least partially within the compartment. The compartment may comprise a recess (as mentioned) that is shaped in accordance with a negative shape of the seal member. Thus, the seal member may be positioned within the recess so that the aperture and the passageway overlap or coincide.

In one embodiment the fastener comprises electronic circuitry. The fastener may further comprise first electrical contacts for contacting with the loudspeaker module. In the hearing protector one or both of the ear cups may have electronic circuitry. Preferably, only one of the ear cups comprises the electronic circuitry (in addition to the loudspeaker module) and the other one of the ear cups is connected to this electronic circuitry. The fastener may for example comprise a printed circuit board or may itself be formed of a printed circuit board.

In a further embodiment the loudspeaker module comprises second electrical contacts. Preferably, the first and second electrical contacts are in releasable contact with each other. The first and/or second electrical contacts may be formed as spring contacts. Thus, a reliable contact can be ensured over a relatively long time. In a preferred embodiment the second electrical contacts are spring contacts and the first electrical contacts are contact pad which the spring contacts contact. Each of the first and second contacts may have a gold coating. The gold coating prevents oxidation of the contacts and minimizes the contact resistance. The loudspeaker module further comprises a loudspeaker, for example a dynamic or an electrodynamic loudspeaker.

In one embodiment the hearing protector comprises a battery. The battery provides for powering any electronic functionality of the hearing protector. The hearing protector may for example have a so-called "listening mode capability". The listing mode capability allows a wearer of the hearing protector to hear sounds from the environment without removing the hearing protector. The sounds provided by the loudspeaker are limited to a maximum noise level of 87 dB (decibels), meaning that the sounds provided by the loudspeaker are within a noise level range of 0 dB to 87 dB but not outside that range. For the listening mode capability the electronic circuitry is configured for amplifying sound signals picked up by a microphone from an area outside of the ear cup. The hearing protector may further have a knob or push button for the wearer to selectively activate and deactivate the listening mode.

The hearing protector may further be configured for radio operation, for example may be connectable or connected to a radio equipment, mobile phone, MP3-player or the like. Such radio operation function may be built-in or provided from external. In the latter case the hearing protector may have a wired or wireless interface (preferably Bluetooth®) for connection with the external device.

In one embodiment the hearing protector has two ear cups being suspended at a headband. The headband is preferably resilient and configured to urge the ear cups toward a wearer's head when the hearing protector is worn.

In a further aspect, the disclosure relates to a method of assembling an ear cup for a hearing protector. The ear cup forms a space for a wearer's ear. The method comprises the steps of:
 providing a shell for forming part of the ear cup, the shell having an ear facing inner side and a passageway extending through the shell between the ear facing inner side and an outer side of the shell;
 providing a loudspeaker assembly comprising a seal member and a loudspeaker module;
 assembling the loudspeaker assembly at the outer side of the shell such that the loudspeaker assembly seals the passageway; and
 retaining the loudspeaker assembly at the shell by a fastener such that a circumferential portion of the seal member is arranged between the shell and the fastener.

In an embodiment the method further comprises the step of pre-assembling the loudspeaker assembly. The loudspeaker module and the seal member thereby may be assembled so that they are retained with each other. This allows for handling the loudspeaker assembly as one piece, for example during manufacturing of the hearing protector.

The fastener may comprise electronic circuitry and first electrical contacts for contacting with the loudspeaker module and the loudspeaker module may comprise second electrical contacts. In a further embodiment the step of retaining the loudspeaker module causes the first and second electrical contacts to get into releasable contact with each other. Therefore separate contacting, for example by soldering or welding, is not required.

DETAILED DESCRIPTION

Figure 1:
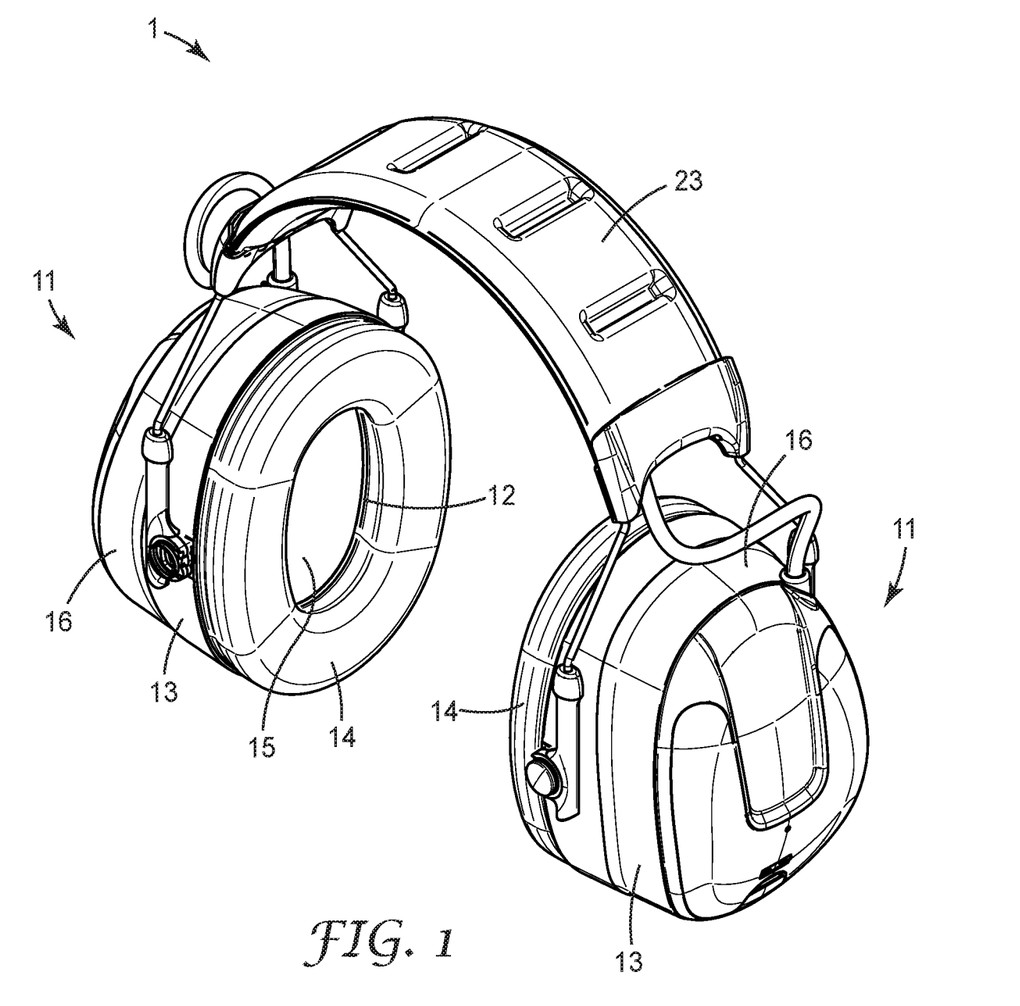
FIG. 1 is a perspective view of a hearing protector according to an embodiment of the disclosure.

FIG. 1 shows a hearing protector 1, in accordance with this disclosure. The hearing protector has two ear cups 11. It is noted that the same numbering (11) used to designate both ear cups does not imply that the ear cups must be identical in every detail, although they can be identical in every detail. In fact, in the present example the two ear cups include certain components that are technically identical and other components that are different as described in the following. The ear cups 11 are suspended at a common headband 23. The headband 23 is resilient and configured to gently urge the ear cups 11 toward a wearer's head when the hearing protector is worn. Further, one of the two ear cups may have additional or fewer components than the other one. The ear cup 11 has a shell 13. In the example the shell 13 is made of a plastic material. The plastic material preferably is generally rigid. Suitable materials are selected from among acrylonitrile-butadiene-styrene terpolymer (ABS), polypropylene (PP), polyethelene (PE), polycarbonate (PC), a blend thereof, and preferably acrylonitrile-butadiene-styrene terpolymer (ABS). Other plastic materials providing the desired rigid structure may be used as appropriate. Each ear cup 11 further has a cushioning 14. The cushioning 14 comprise a soft, preferably elastically deformable material. In the example, the cushioning comprises a foamed polyurethane (PU) core covered by a polyvinylchloride (PVC) sheath. Other materials may be used as appropriate. The cushioning 14 is configured to adapt to a wearer's head in an area around the wearer's ear, so as to form a preferably air-tight seal at this area. Further, the cushioning 14 is ring-shaped and thus provides at least part of a space 12 for the wearer's ear. The ear cup 11 (in interaction with the wearer's head) encapsulates that ear space 12 from the environment by means of at least the cushioning 14 and the shell 11. Each ear cup 11 further has a noise absorber pad 15. The noise absorber pad 15 is preferably made of a foamed material, for example a foamed PU material. The noise absorber pad 15 is preferably retained between the cushioning 14 and an ear facing inner side 22 (indicated in FIG. 2) of the shell 13. It is noted that the term "ear facing inner side" refers to the side of the shell that faces a wearer's ear during normal use of the hearing protector. The cushioning 14 and the shell 13 are preferably removably retained with each other, for example by a snap connection. The noise absorber pad 15 may be clamped between the cushioning 14 and the shell 13. Therefore, the cushioning 14 and the noise absorber pad 15 are exchangeable, for example for the purpose of maintenance or for changing the noise absorbing properties of the hearing protector 1.

Figure 2:
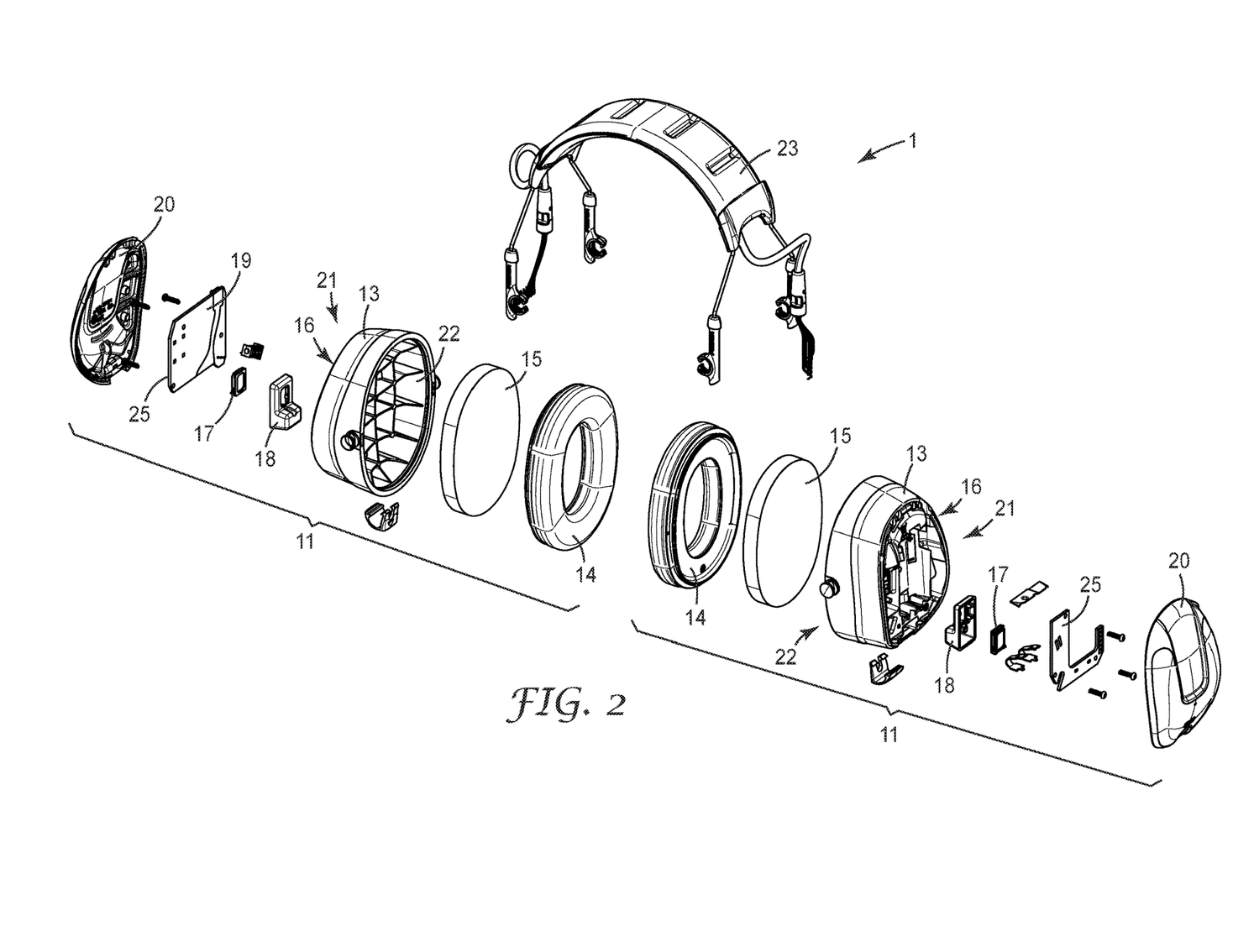
FIG. 2 is an exploded view of the hearing protector shown in FIG. 1.

Referring to FIG. 2 the shell 13 has an outer side 16 which comprises the side which faces in a direction opposite of the ear facing inner side 22 and adjacent lateral sides that face outward. In certain embodiments the outer side 16 may, however, only include the side which faces in a direction opposite of the ear facing inner side 22. In the example each ear cup 11 has a loudspeaker module 17. The loudspeaker module 17 serves for emitting sounds into the ear space 12 so that a wearer of the hearing protector 1 can recognize these sounds despite the noise dampening effect provided by the ear cup 11. The hearing protector 1 as shown in the example may have a listening mode and/or a radio capability. For the listening mode and/or radio capability the hearing protector 1 further has electronic circuitry 19 for amplifying sound signals, for example picked up by a microphone (not shown) or transmitted to the electronic circuitry 19 otherwise. A knob or push button (not shown) may be provided for the wearer to selectively activate and deactivate the listening mode and or radio. The loudspeaker module 17 is assembled to the shell 13 by use of a seal member 18. In particular, the loudspeaker module 17 is arranged within the seal member 18 in an area on the outer side 16 of the shell 13. The seal member 18 and the loudspeaker 17 in combination form a loudspeaker assembly 30, which can be handled in one piece during manufacturing and maintenance of the hearing protector 1. The seal member is preferably made of a silicone material. The silicone material is softer than the material of the shell 13 and resilient. While the skilled person is aware of other soft and resilient materials, silicone has proven to be relatively durable, in particular if kept under a compression force over a long time period.

The hearing protector 1 has further a fastener 25 in each of the ear cups 11 for retaining the respective loudspeaker assembly 30 at the shell 13. In the example at least one of the fasteners comprises the electronic circuitry 19 and is in the form of a printed circuit board. The shell 13 on the outer side 16 forms a compartment 21 which opens in a direction opposite of the direction in which the ear facing inner side 22 faces. The compartment 22 is configured for accommodation of the loudspeaker module 17, the seal member 18, the electronic circuitry 19 and optionally for further components. Each ear cup 11 further has a cover 20 for closing the compartment 22 so as to encapsulate the components accommodated therein.

Figure 3:
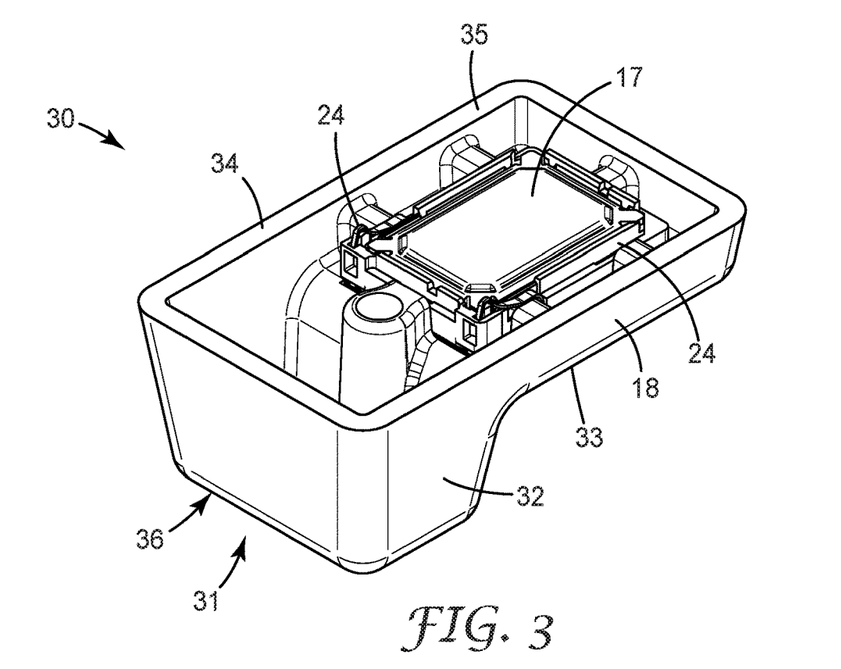
FIG. 3 is a perspective view of a loudspeaker assembly according to an embodiment of the disclosure.

FIG. 3 shows the loudspeaker assembly 30 in more detail. The loudspeaker assembly 30 has the loudspeaker module 17 and the seal member 18.

The loudspeaker module 17 has electrical contacts 24 (also referred to as second electrical contacts herein). In the example the loudspeaker module has two electrical contacts 24. Although the same reference number (24) is used for ease of explanation, the two electrical contacts 24 of the loudspeaker module 17 are mechanically identical but have electrically different functions. The skilled person will be able to select an appropriate loudspeaker module from a variety of loudspeaker modules on the market, including loudspeaker modules having more than two electrical contacts.

The seal member 18 is formed as a tray that has a stepped base wall 31 and a circumferential side wall 32. The stepped configuration of the base wall is preferred, but optional. In accordance with its desired orientation in the hearing protector the base wall 31 is designated to form an "ear facing end" 33 of the seal member 18. The end opposite of the ear facing end 33 is open and therefore is referred to as "open end" 34. The open end 34 is planar which forms a first sealing surface 35 which in the example is planar too. In other words, at the open end 34 the side wall 32 forms a circumferential free end that extends in a plane. The person skilled in the art will recognize that the first sealing surface may have other shapes than planar. For example the sealing surface may be formed as a bulge or ridge extending circumferentially parallel to a plane. The seal member 18 further forms a second sealing surface 36. The sealing surface 36 in the example is formed by outer surfaces of the base wall 31 and the side wall 32. It is noted that the side wall 32 tapers from the open end 34 toward the ear facing end 33.

Figure 4:
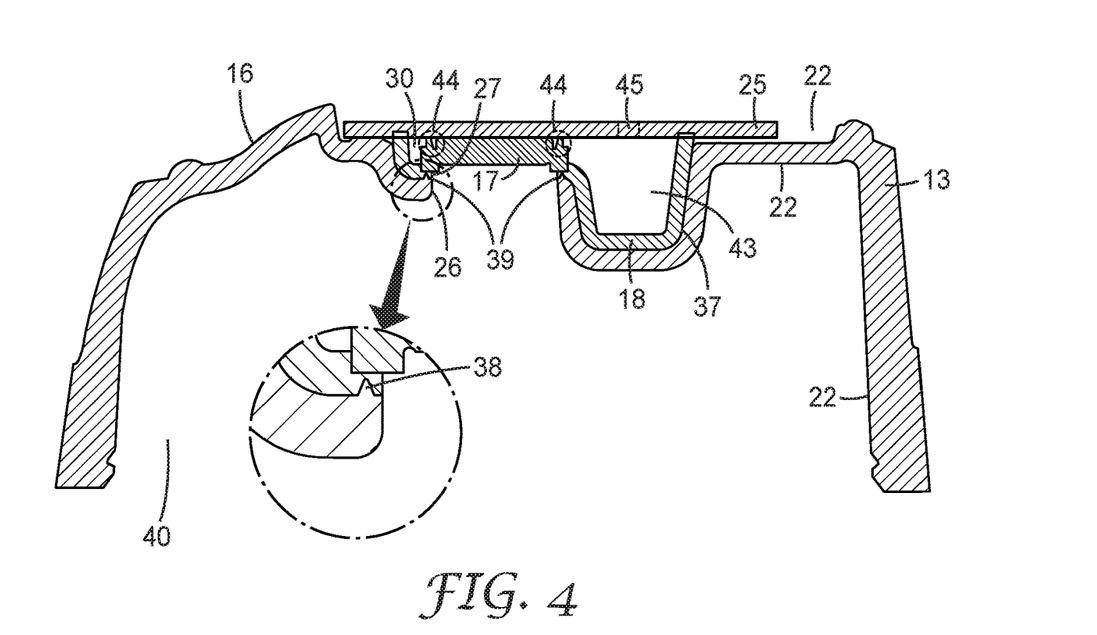
FIG. 4 is a cross-sectional view of an ear cup according to an embodiment of the disclosure.

FIG. 4 shows the loudspeaker assembly 30 assembled in the shell 13. The shell 13 has a passageway 26 extending through the shell 13. The passageway 26 extends in particular between the ear facing inner side 22 and the outer side 16 of the shell. The loudspeaker assembly 30 seals the passageway 26 from the outer side 16. In particular, the loudspeaker assembly 30 blocks the passageway 26 and is removable only in a direction from the ear facing inner side 22 toward the outer side 16 of the shell. Accordingly, the loudspeaker assembly 30 can be assembled only in a direction from the outer side 16 of the shell the ear facing inner side 22 toward the ear facing inner side 22. This enables the loudspeaker assembly and/or the loudspeaker module 17 to be assembled or exchanged in a situation which other components of the ear cup (for example the noise absorber pad and the cushioning) are already assembled at the shell 13.

As described in FIG. 2 the shell forms a compartment 21 (not entirely illustrated in this view) at the outer side 16 of the shell 13. The compartment 21 comprises a recess 37 which is shaped in accordance to a negative outer shape of the seal member 18 (or at least a portion thereof). Further, the passageway 26 is provided within the recess 37. Accordingly, the seal member 18 is (snugly) fit into the recess 37. And thus, the seal member 18—and therefore the loudspeaker assembly 30—are appropriately positioned relative to the passageway 26. The seal member 18 due to the fit within the recess forms a seal in the recess. Further, the shell has a sealing bulge 38. The sealing bulge 38 is located on the outer side 16 of the shell 13. The sealing bulge 38 further entirely surrounds an opening 39 of the passageway 26. The sealing bulge 38 is in a sealing contact with the second sealing surface 36.

Further, the seal member 18 has an aperture 27. The aperture 27 overlaps with the passageway 26 in the situation in which the seal member 18 is fitted in the recess 37. The aperture 27 in the example is closed by the loudspeaker module 17. In particular, the loudspeaker module 17 closes the aperture 27 such that a sound emitting portion of the loudspeaker module 17 faces and overlaps with the aperture 27. Accordingly, any sound emitted by the loudspeaker module 17 is emitted toward a wearer's ear when the hearing protector is worn. It is noted that the skilled person is aware that the passageway 26 and the aperture 27 may in certain examples not be entirely open but may be spanned or provided with a sound permeable material, for example a foamed, woven or non-woven material or a membrane.

As shown, the loudspeaker module 17 is located outside a room 40 that is enclosed or defined by the ear facing inner side of the shell 13. This prevents that any heat generated by the loudspeaker module 17 does not heat up the air around the wearer's ear. Further, this prevents that any moisture, for example due to sweating of the wearer does not easily reach electrical contacts or wires of the loudspeaker module. Accordingly, the arrangement of the loudspeaker module 17 on the outside of the shell 13 helps maximizing the wearing comfort and technical reliability of the hearing protector.

The loudspeaker assembly 30 is retained at the shell via the fastener 25. In particular, the fastener 25 and the shell 13 are retained with each other and clamp the seal member 18 between. Thereby, a circumferential portion of the seal member 18 is arranged between the shell 13 and the fastener 25. That circumferential portion of the seal member 18 further surrounds the passageway 26.

Figure 5:
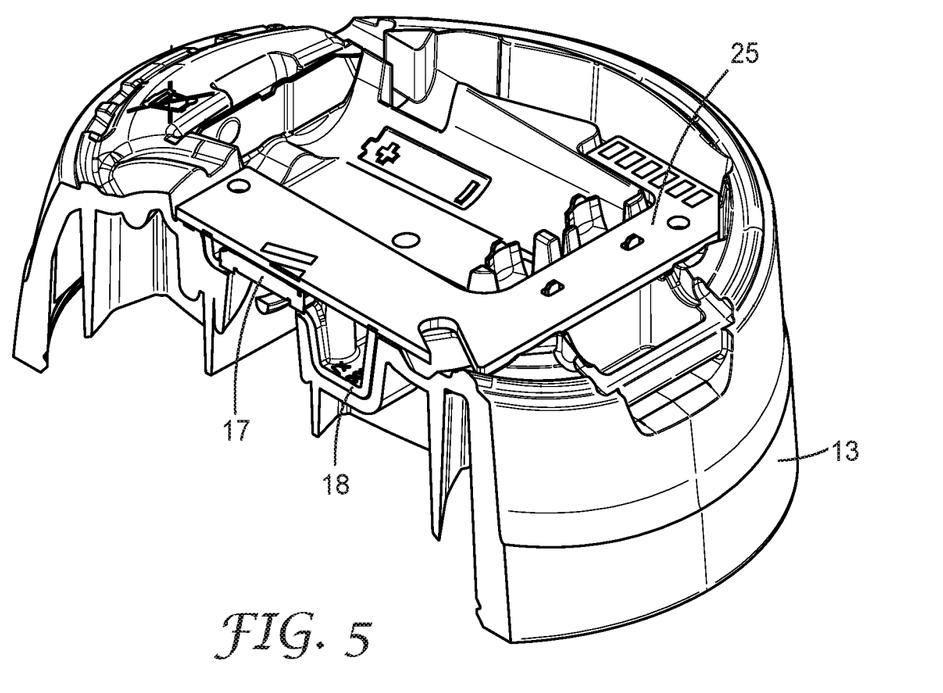
FIG. 5 is a perspective cross-sectional view of an ear cup according to an embodiment of the disclosure.

In the example the fastener 25 further comprises electronic circuitry (indicated in FIG. 5). In particular the electronic circuitry comprises first electrical contacts (not particularly illustrated but indicated by reference number 44). The ear cup (with the shell 13, the loudspeaker assembly 30, and the fastener 25) is configured so that the first electrical contacts 44 meet with the second electrical contacts 24 of the loudspeaker module 17 when the shell 13, the loudspeaker assembly 30, and the fastener 25 are assembled. Further, in the example the fastener 25 and the shell 13 clamp the loudspeaker assembly 30 between. Thus, the loudspeaker assembly 30 is retained in the ear cup under tension. Preferably, thereby also the first and second electrical contacts 24, 44 are held in contact with each other. The first and second electrical contacts 24, 44 are preferably contacted in a releasable contact relationship with each other. Therefore, for example no soldering or welding is required. Further, the first and second electrical contacts 24, 44 are selectively separable from each other as desired, for example during an exchange of the loudspeaker module 17.

The seal member 18 forms a cavity in which the loudspeaker is accommodated. The cavity particularly has a partial volume filled by the loudspeaker volume and a further partial volume which provides a sound volume 43.

The sound volume 43 provides for controlling or determination of the sound frequency profile provided by the loudspeaker assembly 30. In particular the sound frequency profile can be determined by determining the size of the sound volume 43. In the example the sound frequency profile is predetermined by the size of the sound volume 43. The sound volume 43 is delimited by the fastener 25. In the example the fastener 25 hermetically seals the sound volume 43. However, in another example the fastener may have at least one through-hole 45 in fluid communication with the sound volume 43. Such through-hole provides for ventilation of the sound volume 43 and helps keeping a particular sound frequency profile constant under different environmental pressure conditions. In the example the size of the sound may be between 1-2 $cm^3$ depending on speaker size. Generally, a loudspeaker module having a smaller loudspeaker may have smaller sound volume than a loudspeaker module having a greater loudspeaker.

The invention claimed is:

1. A hearing protector having an ear cup forming a space for a wearer's ear, the ear cup comprising:
    a shell having an ear facing inner side and a passageway extending through the shell between the ear facing inner side and an outer side of the shell;
    a loudspeaker assembly, which fits wholly within a shell cavity, and which seals the passageway from the outer side, the loud speaker assembly comprising:
        a loudspeaker module comprising first electrical contacts, wherein the loudspeaker module is positioned within the shell such that sound emitted is emitted toward an ear of a wearer of the hearing protector; and
        a seal member positioned between the loudspeaker assembly and the shell; and
    a fastener that retains the loudspeaker assembly in the shell, wherein the fastener comprises electronic circuitry and second electrical contacts for contacting with the loudspeaker module, and wherein the first and second electrical contacts are in releasable contact with each other.

2. The hearing protector of claim 1, and further comprising a room enclosed or defined by an ear facing inner side of the shell.

3. The hearing protector of claim 2, wherein the room limits heat generated by the loudspeaker module such that heat does not accumulate in the air around the wearer's ear.

4. The hearing protector of claim 3, wherein the room prevents moisture, from the wearer, from reaching the first electrical contacts.

5. The hearing protector of claim 1, wherein the fastener and the shell are retained within each other, such that the seal member is clamped between the fastener and the shell.

6. The hearing protector of claim 5, wherein the loudspeaker assembly is retained in the ear cup under tension and the first and second electrical contacts are held in contact with each other.

7. The hearing protector of claim 1, wherein the seal member comprises the shell cavity, and wherein the loudspeaker module fills a part of the shell cavity, and wherein a remaining part of the shell cavity provides for controlling a sound frequency profile of the loudspeaker assembly.

8. The hearing protector of claim 7, wherein the sound frequency profile is predetermined by the size of the remaining part of the shell cavity.

9. The hearing protector of claim 7, wherein the fastener hermetically seals the remaining part of the shell cavity.

10. The hearing protector of claim 7, wherein the fastener comprises a through-hole in fluid communication with the remaining part of the shell cavity.

11. The hearing protector of claim 1, wherein the seal comprises a soft and resilient material.

12. The hearing protector of claim 11, wherein the seal comprises silicone.

13. A method of assembling an ear cup for a hearing protector, the ear cup forming a space for a wearer's ear, the method comprising the steps of:
   providing a shell for forming part of the ear cup, the shell having an ear facing inner side and a passageway extending through the shell between the ear facing inner side and an outer side of the shell;
   providing a loudspeaker assembly comprising a seal member and a loudspeaker module, wherein the loudspeaker module comprises first electrical contacts;
   assembling the loudspeaker assembly at the outer side of the shell such that the loudspeaker assembly seals the passageway; and
   retaining the loudspeaker assembly at the shell by a fastener such that a circumferential portion of the seal member is arranged between the shell and the fastener, wherein the fastener retains the loudspeaker assembly in the shell, wherein the fastener comprises electronic circuitry and second electrical contacts for contacting with the loudspeaker module, and wherein the first and second electrical contacts are in releasable contact with each other.

\* \* \* \* \*

UNITED STATES PATENT AND TRADEMARK OFFICE
CERTIFICATE OF CORRECTION

PATENT NO. : 10,792,190 B2
APPLICATION NO. : 16/838486
DATED : October 6, 2020
INVENTOR(S) : Johan Håkansson It is certified that error appears in the above-identified patent and that said Letters Patent is hereby corrected as shown below:

On the Title Page

Item (57) (Abstract), Line 6, Delete "loud speaker" and insert -- loudspeaker --, therefor.

In the Specification

Column 1, Line 9, Delete "Apr. 8, 2016," and insert -- Apr. 6, 2017, --, therefor.

Column 1, Line 10, Delete "1614349.9," and insert -- 16164349.9 --, therefor.

Column 1, Line 41, Delete "loud speaker" and insert -- loudspeaker --, therefor.

Column 2, Line 6, Delete "loud speaker" and insert -- loudspeaker --, therefor.

Columns 3-4, Lines 65 (Column 3), Lines 1-4 (Column 4), Delete "The hearing protector may further be configured for radio operation, for example may be connectable or connected to a radio equipment, mobile phone, MP3-player or the like. Such radio operation function may be built-in or provided from external. In the latter case the hearing protector may have a wired or wireless interface (preferably Bluetooth®) for connection with the external device." and insert the same on Column 3, Line 64, as the continuation of same paragraph.

Column 5, Line 5, Delete "polyethelene (PE)," and insert -- polyethylene (PE), --, therefor.

Column 5, Line 54, Delete "and or" and insert -- and/or --, therefor.

In the Claims

Column 8, Line 28, In Claim 1, delete "loud speaker" and insert -- loudspeaker --, therefor.

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*